(12) United States Patent
Rurack et al.

(10) Patent No.: US 8,389,741 B2
(45) Date of Patent: Mar. 5, 2013

(54) DIFLUOROBORADIAZAINDACENE DYES

(75) Inventors: Knut Rurack, Berlin (DE); Ana B. Descalzo, Berlin (DE); Tobias Fischer, Berlin (DE); Thomas Behnke, Berlin (DE)

(73) Assignee: Bam Bundesanstalt fuer Materialforschung und-Pruefung, Berlin (DE)

( * ) Notice: Subject to any disclaimer, the term of this patent is extended or adjusted under 35 U.S.C. 154(b) by 162 days.

(21) Appl. No.: 12/868,810

(22) Filed: Aug. 26, 2010

(65) Prior Publication Data

US 2011/0054187 A1  Mar. 3, 2011

(30) Foreign Application Priority Data

Aug. 28, 2009 (DE) .................. 10 2009 028 982

(51) Int. Cl.
C07D 207/32 (2006.01)
C07F 5/02 (2006.01)

(52) U.S. Cl. ..................................... 548/405

(58) Field of Classification Search .............. 548/405
See application file for complete search history.

(56) References Cited

PUBLICATIONS

Loudet, et al., BODIPY Dyes and their Derivatives: Syntheses and Spectroscopic Properties, Chem. Rev., 2007, 107, p. 4891-4932.
Deniz, et al., Bidirectional Switching of Near IR Emitting Boradiazaindacene Fluorophores, American Chemical Society, vol. 10, No. 16, 2008, p. 3401-3403.
Zheng, et al., Conformationally Restricted Dipyrromethene Boron Difluoride (BODIPY) Dyes: Highly Fluorescent, Multicolored Probes for Cellular Imaging, Chem. Eur. J. 2008, 14, p. 5812-5819.
Erten-Ela, et al., A Panchromatic Boradiazaindacene (BODIPY) Sensitizer for Dye-Sensitized Solar Cells, American Chemical Society, vol. 10, No. 15, 2008, p. 3299-3302.
Ziessel, et al., Solid-State Gas Sensors Developed from Functional Difluoroboradiazaindacene Dyes, Chem. Eur, J., 2009, 15, p. 1359-1369.

*Primary Examiner* — Shawquia Young
(74) *Attorney, Agent, or Firm* — Novak Druce Connolly Bove + Quigg LLP

(57) ABSTRACT

The invention relates to difluoroboradiazaindacene dyes of the formula (1)

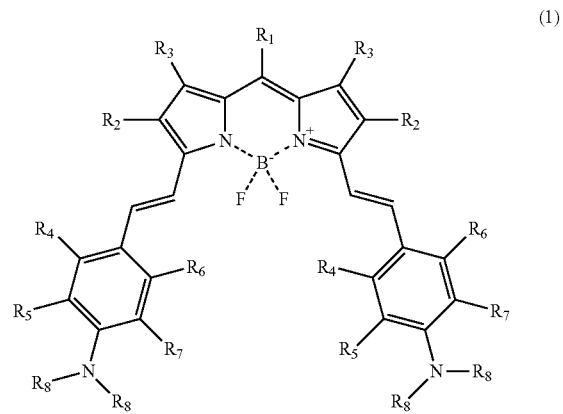

where
$R_1$=fluoro-substituted phenyl residue $C_6H_mF_n$ where n=1 to 5 and m+n=5; or fluoro-substituted naphthyl residue $C_{10}H_mF_n$ where n=1 to 9 and m+n=9;
$R_2$=$CH_3$, $C_2H_5$, $C_3H_7$, or $C_4H_9$;
$R_3$=alkyl, aryl, or vinyl aryl;
$R_4$, $R_5$=H, F, or an $R_4$ and $R_5$ bridging residue CH=CH—CH=CH;
$R_6$, $R_7$=H, F, or an $R_6$ and $R_7$ bridging residue CH=CH—CH=CH; and
$R_8$=alkyl or aryl.

6 Claims, 1 Drawing Sheet

DIFLUOROBORADIAZAINDACENE DYES

CROSS-REFERENCE TO RELATED APPLICATIONS

This application claims the priority of German Application No. 102009028982.8, filed Aug. 28, 2009, the entirety of which is hereby incorporated by reference.

FIELD OF THE INVENTION

The invention relates to novel difluoroboradiazaindacene dyes.

BACKGROUND

Photostable dyes, which exhibit a substantial to highly pronounced absorption in the whole visible spectral range, a moderate to high quantum fluorescence yield, and a large Stokes shift in the near infrared (NIR) spectral range, and exhibit only a weak solvatochromic effect and have no net charge (that is, carry a neutral charge or a zwitterionic charge), are suitable as marker and reference materials in chemical, physical, or biological applications that are based on the measurement of fluorescence signals.

The dyes that are commercially available today are characterized either by (i) narrow and pronounced absorption bands that are in the NIR which exclude an excitation and use in the visible range, have narrow fluorescence bands and small Stokes shifts, and have only low to moderate quantum fluorescence yields and low photostability (for example, cyanine dyes), (ii) by wide absorption bands, but only narrow fluorescence bands that exhibit a small Stokes shift, with low quantum fluorescence yields that deliver only weak signals (for example, porphyrins), (iii) by wide absorption bands and fluorescence bands that exhibit a strong Stokes shift, but only low quantum fluorescence yields and a strong solvatochromic effect, i.e., a high sensitivity to changes in their immediate environment (for example, styryl or oxazine dyes), (iv) by narrow and pronounced absorption bands that are in the NIR which exclude an excitation and use in the visible range, and that have narrow fluorescence bands and small Stokes shifts, but have high quantum fluorescence yields and high photostability (for example, terrylenimide dyes), (v) by good photostability and wide absorption and emission bands, but only low quantum fluorescence yields (for example, quaterrylenebis(dicarboximide) dyes), or (vi) by narrow and pronounced absorption bands that are in the NIR which exclude an excitation and use in the visible range, and that have small Stokes shift and a sensitivity to nucleophilic species (for example, squaraine dyes).

In addition, most of the currently commercially available NIR dyes, with the exception of porphyrins, squaraines, and perylene derivatives, carry a net charge (usually a positive charge), a state that limits their application to polar solvents, materials, and environments.

The results are the following drawbacks:

(i) narrow absorption bands=no possibility of wide-band excitation and use, (ii) small Stokes shifts=only inadequate separation from excitation light/scattering and fluorescence signal possible, (iii) low quantum fluorescence yields=weak fluorescence signals, (iv) low photostability=inadequate service life of the dye or component, and (v) pronounced solvatochromism=undesired signal fluctuation in the event that the environmental parameters change.

The object of the invention is to provide electronically neutral NIR-emitting dyes as potent fluorophores, markers, or reference materials for a wide variety of NIR fluorometric applications, which exhibit better properties, that is, wide-band excitation possibilities, intensive NIR fluorescence, large Stokes shift, high photostability, low solvatochromic effect, and an insensitivity to environmental influences.

In this context, the class of difluoroboryl complexes of dipyrrin (also 4,4-difluoro-4-boro-3a,4a-diaza-s-indacene) is especially important because of the obvious fluorescence of this class of compounds. Representatives of this class of compounds are marketed under the tradename BODIPY (from the English for BOron DIPYrrin) as fluorescence markers for application in the field of molecular biology. In addition to its original use as a biolabel, the dye is also used as a cation sensor, laser dye, and in other fields of the material sciences. The dyes are relatively easily synthetically accessible with a variable substitution pattern and are accessible in preparative quantities. The reason for the multifaceted application and extremely wide spectrum of successful applications of this class of dyes can be attributed to some basic properties, such as high molar extinction coefficient ($\epsilon > 80{,}000$ $M^{-1}$ $cm^{-1}$), high quantum fluorescence yield ($\phi > 0.70$), and moderate redox potential. Representatives of this class of dyes can be found, for example, in U.S. Pat. No. 5,248,782; U.S. Pat. No. 6,005,113; E. Deniz et al., Organic Letters (2008), Vol. 10, No. 16, pages 3401-3403; S. Erten-Ela et al., Organic Letters (2008), Vol. 10, No. 15, pages 3299-3302; Q. Zheng et al., Chem. Eur. J. (2008), No. 14, pages 5812-5819; and Ziessel et al., Chem. Eur. J. (2009), No. 15, pages 1359-1369.

The drawback with the BODIPY dye is that its use is typically limited to a wavelength range between 470 and 530 nm. In addition, a Stokes shift ranging from 5 to 15 nm is a limiting factor for many applications. In particular, this property is a drastic disadvantage for use in single molecule spectroscopy and in multiplexing applications.

SUMMARY OF THE INVENTION

The invention intends to solve one or more of the aforementioned problems or at least minimize them. To this end, the invention provides the following difluoroboradiazaindacene dyes of the formula (1):

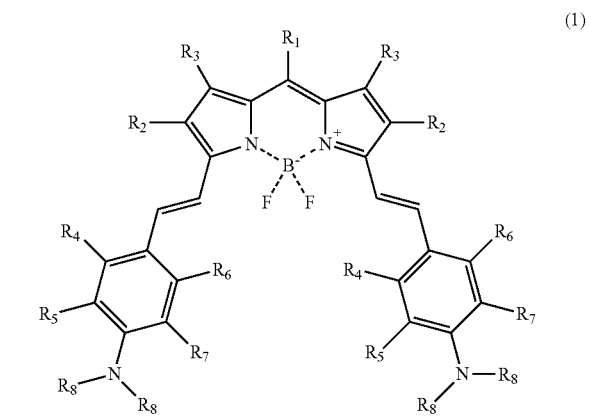

where $R_1$ = fluoro-substituted phenyl residue $C_6H_mF_n$ where n=1 to 5 and m+n=5; or fluoro-substituted naphthyl residue $C_{10}H_mF_n$ where n=1 to 9 and m+n=9;

$R_2$ = $CH_3$, $C_2H_5$, $C_3H_7$, or $C_4H_9$;

$R_3$ = alkyl, aryl, or vinyl aryl;

$R_4$, $R_5$ = H, F, or an $R_4$ and $R_5$ bridging residue CH=CH—CH=CH;

$R_6$, $R_7$ = H, F, or an $R_6$ and $R_7$ bridging residue CH=CH—CH=CH; and $R_8$ = alkyl or aryl.

Preferably, $R_1$ is $C_6F_5$.

Furthermore, preferred is when $R_3$ is $CH_3$, in particular also in combination with the above-described preferred embodiments.

Moreover, preferred is when $R_4$ and $R_5$ are a bridging residue CH=CH—CH=CH, in particular also in combination with the above-described preferred embodiments.

Especially preferred are the difluoroboradiazaindacene dyes of the formulas (2) and (3):

(2)

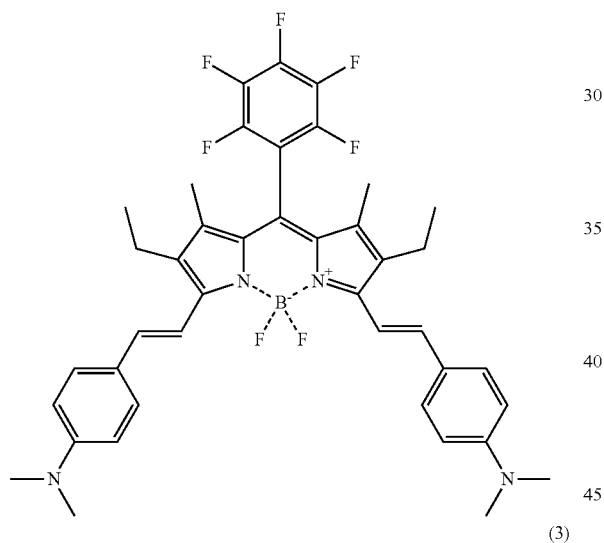

(3)

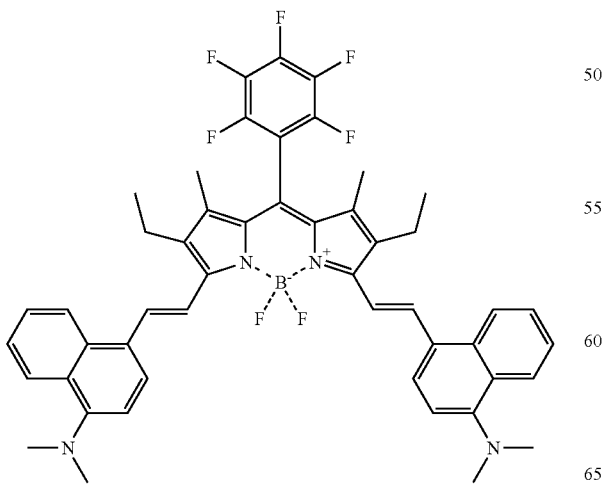

The dyes can generally be used in direct, indirect, and highly polar environments and media, irrespective of whether they are dissolved in molecular form or encapsulated in particles or other materials.

DETAILED DESCRIPTION OF THE INVENTION

The invention is explained in detail below by means of two embodiments, dnBDP5F (corresponding to formula (3)) and dsBDP5F (corresponding to formula (2)), and the associated precursor BDP5F (see scheme 1).

Scheme 1

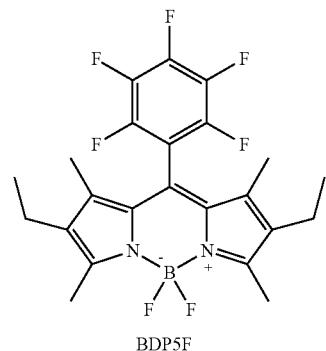

BDP5F

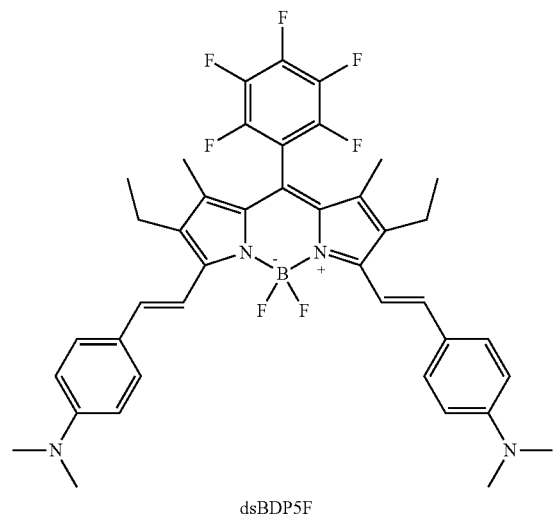

dsBDP5F

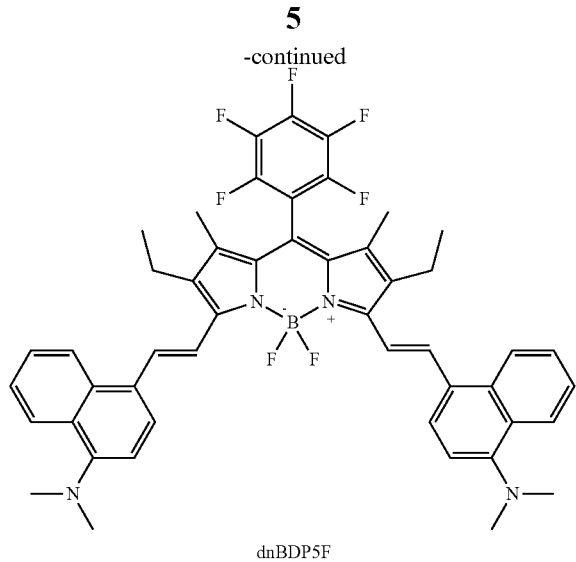

dnBDP5F

Figure 1A:
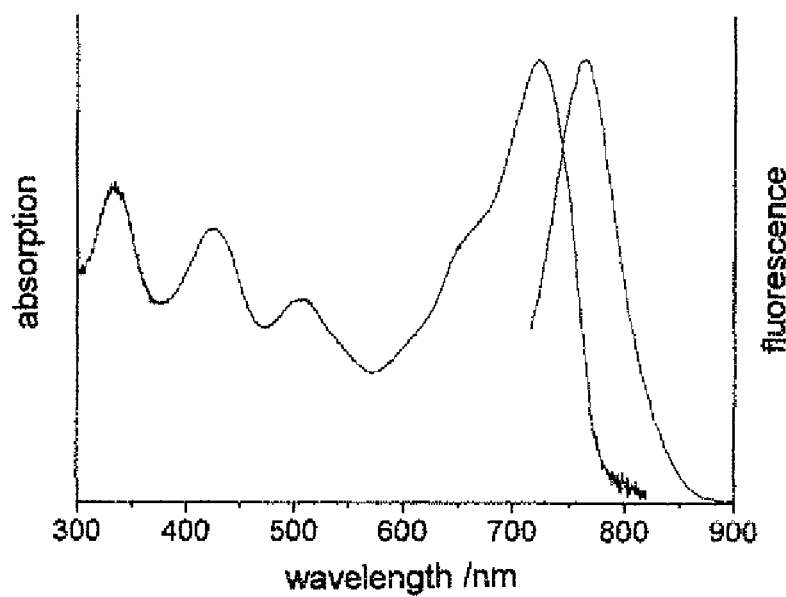
FIG. 1A is a representative spectra of dsBDP5F.
Figure 1B:
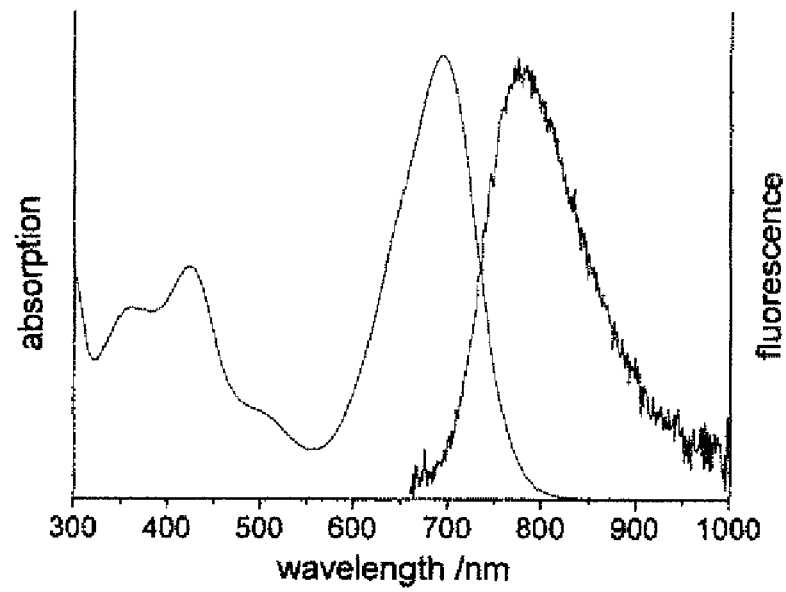
FIG. 1B is a representative spectra of dnBDP5F.

FIGS. 1A and 1B show the absorption and fluorescence spectra of the dyes dnBDP5F and dsBDP5F in diethyl ether.

EXPERIMENTAL PART

All of the reagents come from commercial manufacturers and were used without any additional purification, provided it is not stated otherwise. All of the air and humidity-sensitive reactions were carried out under argon atmosphere in dry glass apparatuses. Dichloromethane was distilled over calcium hydride, and triethylamine was purified by distillation. The NMR spectra were measured with 400 and 600 MHz equipment from Bruker.

Preparation of the Precursor BDP5F 3-ethyl-2,4-dimethylpyrrole (369.6 mg, 3 mmol) and 2,3,4,5,6-pentafluorobenzaldehyde (353.0 mg, 1.8 mmol) were dissolved in dry $CH_2Cl_2$ (70 mL) under argon atmosphere. A drop of trifluoroacetic acid (TFA) was added, and the solution was stirred for 5 hours at room temperature in the dark. 2,3-dichloro-5,6-dicyano-1,4-benzoquinone (DDQ, 408.6 mg, 1.8 mmol) were added, and the mixture was stirred for another 30 minutes. Then the reaction mixture was treated with triethylamine (4 mL) and boron trifluoride ethyl etherate (4 mL). After another 30 minutes of stirring, the deep red solution was washed with water (3×50 mL) and dichloromethane (50 mL), dried over $Na_2SO_4$, and concentrated under reduced pressure. The raw product was purified by column chromatography over silica gel (50% v/v $CH_2Cl_2$/hexane) and recrystallized from hexane. The resulting yield was reddish orange crystals (166 mg; 20% yield).

NMR: $^1$H-NMR (400 MHz, $CDCl_3$) [ppm] δ=2.55 (s, 6H, $CH_3$), 2.34 (q, J=7.6 Hz, 4H, $CH_2$), 1.51 (s, 6H, $CH_3$), 1.02 (t, J=7.6 Hz, 6H, $CH_3$).

Preparation of dnBDP5F and dsBDP5F

In general, the corresponding aldehydes and BDP5F were heated under reflux for 26 hours in a solvent mixture of dry toluene (5 mL), glacial acetic acid (0.15 mL), and piperidine (0.18 mL) with a small addition of a molecular sieve of 4 angstrom pore size. After cooling to room temperature, the solvent was removed under vacuum, and the raw product was eluted with 50% v/v $CH_2Cl_2$/hexane over a silica column.

dsBDP5F: 19.2 mg (0.13 mmol) of 4-dimethylaminobenzaldehyde and 30 mg (0.06 mmol) of BDP5F delivered dsBDP5F as a brown powder. Yield 2%.

$^1$H-NMR (600 MHz, $CDCl_3$) [ppm] δ=7.63 (d, J=16.7 Hz, 2H, CH), 7.54 (d, J=8.9 Hz, 4H, CH), 7.23 (d, J=16.7 Hz, 2H, CH), 6.74 (d, J=8.9 Hz, 4H, CH), 3.03 (s, 12H $CH_3$), 2.64 (q, J=7.6 Hz, 4H, $CH_2$), 1.57 (s, 6H, $CH_3$), 1.19 (t, J=7.6 Hz, 6H, $CH_3$).

dnBDP5F: 37.3 mg (0.187 mmol) of 4-dimethylamino)-1-naphthaldehyde and 38.3 mg (0.08 mmol) of BDP5F delivered dnBDP5F as a green solid. Yield 1%.

$^1$H-NMR (600 MHz, $CDCl_3$) [ppm] δ=8.26 (m, 2H, CH), 8.17 (m, 2H, CH), 8.15 (d, J=16.9 Hz, 2H, CH), 7.96 (d, J=7.9 Hz, 2H, CH), 7.80 (d, J=16.4 Hz, 2H, CH), 7.52 (m, 4H, CH), 7.16 (d, J=7.9 Hz, 2H, CH), 2.95 (s, 12H, $CH_3$), 2.75 (q, J=7.5 Hz, 4H, $CH_2$), 1.65 (s, 6H, $CH_3$), 1.31 (t, J=7.5 Hz, 6H, $CH_3$).

Photostability Tests

The photostability tests were conducted with a 150 W xenon lamp, with which a 1 mm cuvette was irradiated at 670 nm using a slit width of 15 nm. The light beam was focused on a 1.5 $cm^2$ area of the cuvette. The transmission was detected with a 600 nm filter. 300 μL of the dye solution with a concentration of $1.8 \times 10^{-5}$ mmol $L^{-1}$ (dnBDP5F) and $3.5 \times 10^{-5}$ mmol $L^{-1}$ (dsBDP5F) in THF, equivalent to an optical density of 0.08 or 0.05 respectively, were used as the samples. The irradiation was limited to 17 hours with an average irradiation intensity of 0.5 mW $cm^{-2}$. The irradiation energy was measured with a calibrated Si diode, in order to determine the number of transmitted and absorbed photons. On the basis of the measurements, the decrease in the concentration was calculated according to the Beer-Lambert law.

Representative spectra and spectroscopic data of dsBDP5F and dnBDP5F are listed in the Tables 1 and 2 and FIGS. 1A and 1B.

Spectroscopic data of dsBDP5F in various solvents at 298 K, a dye concentration of $2 \times 10^{-6}$ M, and under excitation at $\lambda^{ex}$=670 nm (n.s.=not adequately soluble):

TABLE 1

| Solvent | $\lambda_{abs}$/nm | $\lambda_{em}$/nm | $\Delta\nu_{abs-em}$/$cm^{-1}$ | $\Phi_f$ |
| --- | --- | --- | --- | --- |
| Hexane | n.s. | n.s. | — | — |
| Dibutyl ether | 723 | 763 | 750 | 0.43 |
| Diethyl ether | 723 | 772 | 890 | 0.18 |
| THF | 739 | 792 | 900 | 0.11 |

Spectroscopic data of dnBDP5F in various solvents at 298 K, a dye concentration of $2 \times 10^{-6}$ M, and under excitation at $\lambda_{ex}$=640 nm:

TABLE 2

| Solvent | $\lambda_{abs}$/nm | $\lambda_{em}$/nm | $\Delta\nu_{abs-em}$/$cm^{-1}$ | $\Phi_f$ |
| --- | --- | --- | --- | --- |
| Hexane | 692 | 742 | 980 | 0.23 |
| Dibutyl ether | 697 | 766 | 1290 | 0.17 |
| Diethyl ether | 696 | 779 | 1530 | 0.13 |
| THF | 699 | 827 | 2210 | 0.06 |

Representative molar absorption coefficients and data on the photostability were obtained for dsBDP5F and dnBDP5F in THF. The excellent photostability of the dyes is reflected especially in the decrease of only 1% for dsBDP5F and 2% for dnBDP5F of the dye absorption after 17 hours of irradiation. It is assumed that the effect is due to, among other things, the use of the pentafluorophenyl residue in the meso position. Table 3 compares the spectroscopic data of BDP5F and its phenyl analog, 1,3,5,7-tetramethyl-2,6-diethyl-8-phenyl-4-difluorobora-3a,4a-diaza-(s)-indacene (BDP5H) in selected solvents at 298 K, a dye concentration of $2 \times 10^{-6}$ M, and under excitation at $\lambda_{ex}$=500 nm.

TABLE 3

| | Solvent | $\lambda_{abs}$/nm | $\lambda_{em}$/nm | $\Delta\nu_{abs-em}$/cm$^{-1}$ | $\Phi_f$ |
|---|---|---|---|---|---|
| BDP5F | Dibutyl ether | 543 | 557 | 460 | 0.95 |
| | Diethyl ether | 541 | 557 | 530 | 1.00 |
| BDP5H | Dibutyl ether | 524 | 535 | 390 | 0.78 |
| | Diethyl ether | 522 | 535 | 460 | 0.77 |

The invention claimed is:

1. A difluoroboradiazaindacene dye of the formula (1)

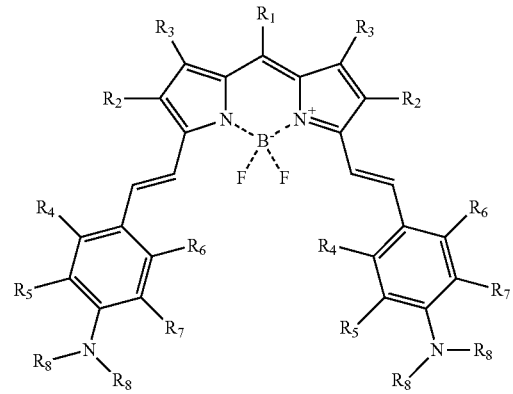

(1)

where
- $R_1$ = fluoro-substituted phenyl residue $C_6H_mF_n$ where n=1 to 5 and m+n=5; or fluoro-substituted naphthyl residue $C_{10}H_mF_n$ where n=1 to 9 and m+n=9;
- $R_2$ = $CH_3$, $C_2H_5$, $C_3H_7$, or $C_4H_9$;
- $R_3$ = alkyl, aryl, or vinyl aryl;
- $R_4$, $R_5$ = H, F, or an $R_4$ and $R_5$ bridging residue CH=CH—CH=CH;
- $R_6$, $R_7$ = H, F, or an $R_6$ and $R_7$ bridging residue CH=CH—CH=CH; and
- $R_8$ = alkyl or aryl.

2. The difluoroboradiazaindacene dye according to claim 1, wherein $R_1$ is $C_6F_5$.

3. The difluoroboradiazaindacene dye according to claim 1, wherein $R_3$ is $CH_3$.

4. The difluoroboradiazaindacene dye according to claim 1, wherein $R_4$ and $R_5$ are a bridging residue CH=CH—CH=CH.

5. A difluoroboradiazaindacene dye of the formula (2)

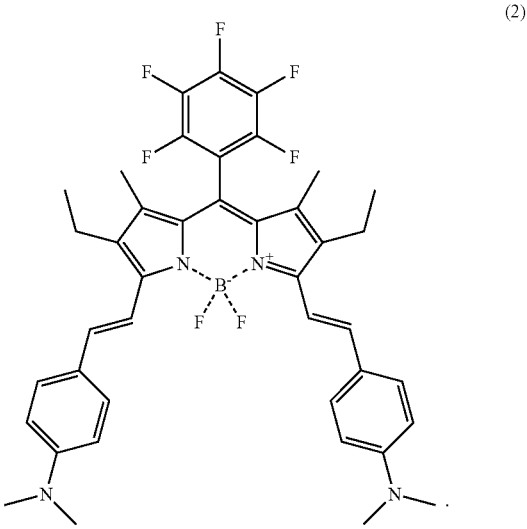

(2)

6. A difluoroboradiazaindacene dye of the formula (3)

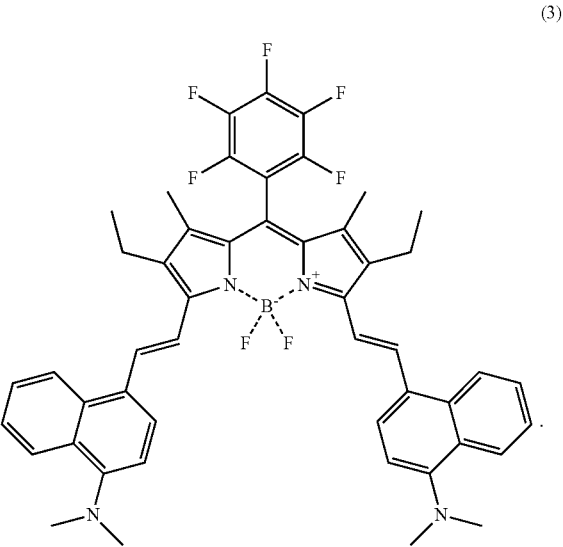

(3)

* * * * *